United States Patent
Miller et al.

(10) Patent No.: US 10,227,365 B2
(45) Date of Patent: Mar. 12, 2019

(54) PREVENTING SOLVENT OF CRYSTALLIZATION IN PRODUCTION OF POLYPHOSPHITE LIGANDS

(71) Applicant: Dow Technology Investments LLC, Midland, MI (US)

(72) Inventors: Glenn A. Miller, South Charleston, WV (US); Pramod Dalvi, Mumbai (IN); Ravindrakumar N. Raval, Ahmedabad (IN)

(73) Assignee: Dow Technology Investments LLC, Midland, MI (US)

( * ) Notice: Subject to any disclaimer, the term of this patent is extended or adjusted under 35 U.S.C. 154(b) by 535 days.

(21) Appl. No.: 14/355,392

(22) PCT Filed: Oct. 25, 2012

(86) PCT No.: PCT/US2012/061874
§ 371 (c)(1),
(2) Date: Apr. 30, 2014

(87) PCT Pub. No.: WO2013/066712
PCT Pub. Date: May 10, 2013

(65) Prior Publication Data
US 2014/0288322 A1    Sep. 25, 2014

(30) Foreign Application Priority Data

Oct. 31, 2011  (IN) .......................... 3721/CHE/2011

(51) Int. Cl.
*C07F 9/08*     (2006.01)
*C07F 9/6574*   (2006.01)

(52) U.S. Cl.
CPC ................. *C07F 9/65746* (2013.01)

(58) Field of Classification Search
CPC ....................................................... C07F 9/08
See application file for complete search history.

(56) References Cited

U.S. PATENT DOCUMENTS

| | | | |
|---|---|---|---|
| 4,182,704 A | | 1/1980 | Spivack |
| 4,318,845 A | * | 3/1982 | Spivack .............. C07F 9/65744 524/100 |
| 4,351,759 A | * | 9/1982 | Spivack ........................ 524/100 |
| 4,769,498 A | | 9/1988 | Billig et al. |
| 5,235,113 A | | 8/1993 | Sato et al. |
| 5,288,918 A | | 2/1994 | Maher et al. |
| 5,334,739 A | | 8/1994 | Pastor et al. |
| 5,391,801 A | | 2/1995 | Sato et al. |
| 5,688,986 A | | 11/1997 | Tam et al. |
| 5,741,942 A | | 4/1998 | Bryant et al. |
| 2007/0112219 A1 | | 5/2007 | Ortmann et al. |
| 2010/0267991 A1 | | 10/2010 | Ritter et al. |
| 2013/0317246 A1 | | 11/2013 | Kreidler et al. |

FOREIGN PATENT DOCUMENTS

| | | |
|---|---|---|
| EP | 0026893 A1 | 4/1981 |
| EP | 0518241 A2 | 12/1992 |
| WO | 93/03839 A1 | 3/1993 |
| WO | 2010/042313 A1 | 4/2010 |

OTHER PUBLICATIONS

EP0026893—machine-translation, 1981, machine translation of EP0026893.*

* cited by examiner

*Primary Examiner* — Sun Jae Yoo
(74) *Attorney, Agent, or Firm* — Husch Blackwell LLP

(57) ABSTRACT

Residual wash solvent, e.g., ethyl acetate, is removed from polyphosphite, e.g., bisphosphite, crystals by a process comprising the steps of: A. Mixing the polyphosphite crystals and residual wash solvent with a secondary alcohol, e.g., isopropyl alcohol (IPA), to form a mixture of polyphosphite crystals, residual wash solvent and secondary alcohol, and B. Drying the mixture to remove the residual wash solvent and secondary alcohol to a content of less than 0.5 wt % based on the weight of the polyphosphite crystals.

6 Claims, No Drawings

PREVENTING SOLVENT OF CRYSTALLIZATION IN PRODUCTION OF POLYPHOSPHITE LIGANDS

BACKGROUND OF THE INVENTION

1. Field of the Invention

This invention relates to polyphosphite ligands. In one aspect the invention relates to the manufacture of polyphosphite ligands while in another aspect, the invention relates to removing residual solvent from finished polyphosphite ligand product.

2. Description of the Related Art

The preparation of polyphosphite ligands is well known and is described in, among other references, U.S. Pat. Nos. 4,769,498 and 5,688,986, US 2007/0112219 and WO 93/03839. The condensation reactions of these processes are typically performed in an inert hydrocarbon solvent, e.g., toluene, and produce polyphosphite crystals. The solvent is removed from the crystals by any convenient means, e.g., distillation, and then the crystals are dissolved in a second or wash solvent, e.g., ethyl acetate, to remove impurities. The polyphosphite is then re-crystallized from the second solvent and recovered by conventional means, e.g., centrifugation with the impurities remaining in the solvent.

Over the past 20 years or so, different manufacturing entities have experienced difficulties in the last step in the production of polyphosphite, i.e., the removal of the wash solvent from which the polyphosphite is re-crystallized. This step usually requires drying the product to less than (<) 0.5 weight percent (wt %) residual wash solvent. In some cases, extreme vacuum and elevated temperatures are required to dry the material and sometimes even 300 hours of drying is insufficient to meet specification. Residual wash solvent, even at these relatively low levels, can render the polyphosphite more vulnerable to degradation during storage and introduce unwanted variability in the final product. If the solvent is ethyl acetate, in some applications it can be considered a contaminate, particularly in pharmaceutical applications.

Without being bound by theory, centrifugation or high pressure filtration may compress the crude polyphosphite crystals and cause the formation of classical solvent of crystallization. Traditionally heating under vacuum is the conventional means to break a solvent of crystallization. However, this detail is not discussed in the art because laboratory testing of conditions and equipment used in the manufacture of polyphosphites does not exhibit solvent of crystallization. Strangely, this phenomenon appears to be limited to commercial operations and unless investigators are involved in scaling up a laboratory manufacturing process for polyphosphite production to a commercial process, they are not likely to observe the problem.

SUMMARY OF THE INVENTION

In one embodiment the invention is a process for removing residual wash solvent from polyphosphite crystals.

In one embodiment the invention is a process for removing residual wash solvent, e.g., ethyl acetate, from polyphosphite, e.g., bisphosphite, crystals, the process comprising the steps of:

A. Mixing the polyphosphite crystals and residual wash solvent with a secondary alcohol, e.g., isopropyl alcohol (IPA), to form a mixture of polyphosphite crystals, residual wash solvent and secondary alcohol, and B. Drying the mixture to remove the residual wash solvent and secondary alcohol to a content of less than 0.5 wt % based on the weight of the polyphosphite crystals.

In one embodiment the crystals are first removed from the mixture and then dried.

DETAILED DESCRIPTION OF THE PREFERRED EMBODIMENT

Definitions

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, molecular weight, etc., is from 100 to 1,000, then all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, the relative amounts of secondary alcohol to use in the mixing with residual solvent and polyphosphite crystals.

"Wash solvent", "second solvent" and like terms mean the solvent used to remove from the polyphosphite crystals impurities and other materials of the condensation reaction(s) from which the polyphosphite crystals are made. The condensation reactions are performed in a first solvent, e.g., toluene, which is removed at the completion of the reaction by any conventional means, e.g., distillation, and this leaves the by-products, unreacted reagents and other components of the reaction mass with the product crystals. The purpose of the wash solvent is to remove these other materials from the finished crystal product, or at least reduce the amount of these other materials associated with the finished crystal product.

"Residual wash solvent" and like terms mean the amount of wash solvent remaining with the polyphosphite crystals after the crystals have been separated from the solvent, typically by centrifugation. The amount of solvent remaining is typically greater than (>) 0.5 wt % (based on the weight of the crystals), even after substantial effort to evaporate the solvent under vacuum. While the typical practice of this invention is to reduce the amount of residual wash solvent to as small amount as practical using conventional rotary dried equipment and protocol, the amount of residual wash solvent can be such as to slurry the crystals.

"Polyphosphite crystals" and like terms mean the product of the condensation reaction(s) used to make the polyphosphite. While the morphology and size of the crystals will vary with the composition of the polyphosphite and conditions under which it was made, typical bisphosphite crystals range from amorphous crystalline powders (average particle size of 25 microns) to well-formed platelets of 180 microns or more. Experience suggests that the larger the crystals, the greater the problem of residual wash solvent.

Polyphosphite Ligands

The polyphosphite ligands used in the practice of this invention are known compounds, and have the general formula.

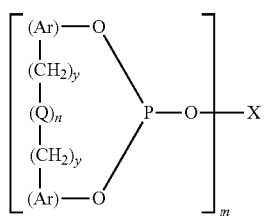

(i)

wherein each Ar group represents an identical or different substituted or unsubstituted aryl radical; wherein X represents a m-valent radical selected from the group consisting of alkylene, alkylene-oxy-alkylene, arylene, and arylene-$(CH_2)y$--$(Q)_n$-$(CH_2)y$-arylene-, wherein each arylene radical is the same as Ar defined above (i.e., each arylene may represent an identical or different, substituted or unsubstituted arylene radical); wherein each y individually has a value of 0 or 1; wherein each Q individually represents a divalent bridging group selected from the class consisting of —$CR_1R_2$—, —O—, —S—, —$NR_3$—, —$SiR_4R_5$~ and —CO—, wherein each $R_1$ and $R_2$ radical individually represents a radical selected from the group consisting of hydrogen, aikyl of 1 to 12 carbon atoms, phenyl, tolyl and anisyl, wherein each $R_3$, $R_4$, and $R_5$ radical individually represents —H or —$CH_3$; wherein each n individually has a value of 0 or 1; and wherein m has a value of 2 to 6, preferably 2 to 4. Preferably each y and each n has a value of 0. Moreover, when either n is 1, its corresponding Q is preferably a-$CR_1R_2$— bridging group as defined above and more preferably methylene (—$CH_2$—) or alkylidene (—$CHR_2$—), wherein $R_2$ is an alkyl radical of 1 to 12 carbon atoms, (e.g. methyl, ethyl, propyl, isopropyl, butyl, isodecyl, dodecyl, etc., especially methyl).

Illustrative m-valent radicals represented by X in the above polyphosphite formula include substituted and unsubstituted radicals selected from the group consisting of alkylene, alkylene-oxy-alkylene, phenylene, naphthylene, phenylene —$(CH_2)_y(Q)_n$-$(CH_2)_y$-phenylene and naphthylene-$(CH_2)_y(Q)_m(CH_2)_y$-naphthylene-radicals, Q, n and y are the same as defined above. More specific illustrative m-valent radicals represented by X include e.g. straight or branched chain alkylene radicals such as —$(CH_2)_x$ wherein x has a value of 2 to 18 (preferably 2 to 12), pentaerythritol,1,2,6-hexylene, and the like; —$CH_2CH_2OCH_2CH_2$—, 1,4-phenylene, 2,3-phenylene, 1,3,5-phenylene, 1,3-phenylene, 1,4-naphthylene, 1,5-naphthylene, 1,8-naphthylene, 2,3-naphthylene, 1,1'biphenyl-2,2'-diyl, 2,2'biphenyl-1,1'-diyl, 1,1'-biphenyl-4,4'-diyl, 1,1'binaphthyl-2,2'-diyl, 2,2'-binaphthyl-1,1'-diyl, phenylene-$CH_2$-phenylene, phenylene-S-phenylene, $CH_2$-phenylene-$CH_2$, phenylene-$CH(CH_3)$— phenylene radicals and the like.

Thus X is an m-valent radical which may contain from 2 to 30 carbon atoms, wherein the alkylene and alkylene-oxyalkylene radicals preferably contain from 2 to 18 and more preferably from 2 to 12 carbon atoms, while the arylene type radicals may contain from 6 to 18 carbon atoms. Preferably X is ethylene or an arylene type radical and more preferably a naphthylene or a substituted or unsubstituted phenylene-$(Q)_n$-phenylene radical.

Illustrative aryl radicals represented by the Ar groups and the arylene radicals of X in the above polyphosphite formula include both substituted and unsubstituted aryl radicals. Such aryl radicals may contain from 6 to 18 carbon atoms such as phenylene ($C_6H_4$), naphthylene ($C_{10}H_6$), anthracylene ($C_{14}H_8$), and the like.

Among the more preferred polyphosphite ligands are those wherein the two Ar groups linked by the bridging group represented by —$(CH_2)_y$-$(Q)_n$-$(CH_2)_y$— in Formula I above are bonded through their ortho positions in relation to the oxygen atoms that connect the Ar groups to the phosphorus atom. It is also preferred that any substituent radical, when present on such Ar groups be bonded in the para and/or ortho position of the aryl in relation to the oxygen atom that bonds the given substituted Ar group to its phosphorus atom.

Accordingly, a preferred class of polyphosphite ligands employable in this invention are those of the formulas

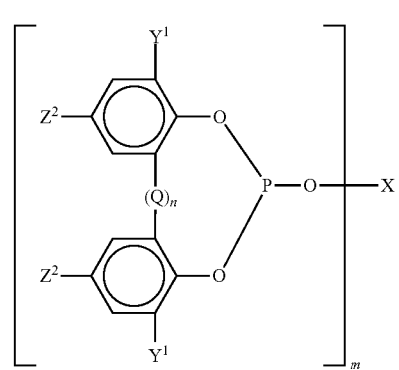

(ii)

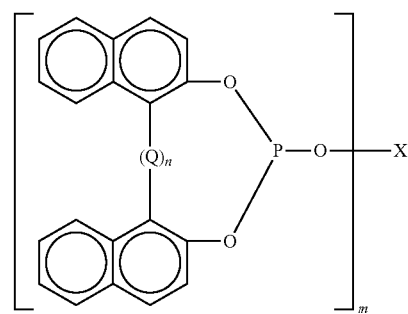

(iii)

wherein in Formulas (II) and (III), Q is —$CR_1R_2$— wherein each $R_1$ and $R_2$ radical individually represents a radical selected from the group consisting of hydrogen, alkyl of 1 to 12 carbon atoms (e.g. methyl, propyl, isopropyl, butyl, isodecyl, dodecyl, etc.) phenyl, tolyl and anisyl, and n has a value of 0 to 1; wherein each $Y_1$, $Y_2$, $Z_2$, and $Z_3$ group individually represents a radical selected from the group consisting of hydrogen, an alkyl radical having from 1 to 18 carbon atoms, substituted or unsubstituted aryl, alkaryl, aralkyl and alicyclic radicals as defined and exemplified herein (e.g. phenyl, benzyl, cyclohexyl, 1-methylcyclohexyl, and the like), cyano, halogen, nitro, trifluoromethyl, hydroxy, as well as the carbonyloxy, amino, acyl, phosphonyl, oxycarbonyl, amido, sulfinyl, sulfonyl, silyl, alkoxy, and thionyl as defined and exemplified herein, and wherein m has a value of 2 to 6, more preferably 2 to 4 and most preferably 2, and wherein X is a m-valent radical as generically and preferably herein defined. Preferably both $Y_1$ and $Y_2$ are radicals having a steric hindrance of isopropyl, or more preferably t-butyl, or greater. Preferably Q represents a methylene (—$CH_2$—) bridging group or an alkylidene (—$CHR_2$—) bridging group wherein $R_2$ is an alkyl radical of 1 to 12 carbon atoms as defined above, especially methyl (e.g. —$CHCH_3$—). The more preferred ligands are those of Formula (II) above, wherein, both Y and $Y_2$ are branched chain alkyl radicals having three to five carbon atoms, especially t-butyl, and $Z_2$ and $Z_3$ are hydrogen, an alkyl radical, especially t-butyl, a hydroxy radical or an alkoxy radical, especially methoxy.

Further more preferred polyphosphite ligands include those wherein X in the above polyphosphite formulas is a divalent radical selected from the group consisting of alkylene, especially ethylene, alkylene-oxy-alkylene, especially $CH_2CH_2OCH_2CH_2$, and substituted or unsubstituted phenylene, naphthylene, naphthylene-$(Q)_n$-naphthylene and phenylene-$(Q)_n$-phenylene radicals wherein Q and n are the same as both generically and preferably defined above. Among the more preferred bisphosphite type ligands when m is 2 are those wherein X is a divalent radical selected from the group consisting of 1,2-ethylene, naphthylene, substituted phenylene and substituted phenylene-$(Q)_n$-phenylene radicals, especially 1,4-naphthylene and 1,5-naphthylene. Moreover the preferred substituents on such phenylene and/or phenylene-$(Q)_n$-phenylene radicals are preferably radicals selected from the group consisting of alkyl and alkoxy radicals, which most preferably correspond to the substituent radicals of $Y_1$, $Y_2$, $Z_2$ and $Z_3$ defined herein.

Another preferred class of bisphosphite ligands that can be used in the practice of this invention is described in U.S. Pat. Nos. 4,769,498 and 5,741,942.

Another group of polyphosphite ligands used in the practice of this invention are known compounds described in U.S. Pat. Nos. 5,235,113 and 6,031,120, and have the general formulas.

$$[(R_1O)(R_2O)PO]m—X \qquad (v)$$

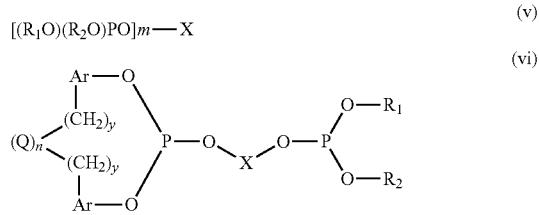

(vi)

where m, n, X, y, Ar, $R_1$ and $R_2$ are as defined above. Preferably, $R_1$ and $R_2$ are substituted or unsubstituted aryl, substituted or unsubstituted phenylene, and/or substituted or unsubstituted naphthylene moieties.

The methods for preparing the polyphosphite ligands described above and employable in this invention are known. For instance, these polyphosphite ligands can be readily and easily prepared via a series of conventional phosphorus halide-alcohol condensation reactions. Such types of condensation reactions and the manner in which they may be conducted are well known in the art. For instance a simple method for preparing such ligands comprises (a) reacting a corresponding organic diphenolic compound with phosphorus trichloride to form the corresponding organic phosphorochloridite intermediate, (b) reacting the intermediate with a diol (corresponding to X in the above formulas) to form the corresponding hydroxy substituted diorganophosphite intermediate, (c) reacting the diorganophosphite intermediate with phosphorus trichloride to form the corresponding phosphorodichloridite intermediate, and (d) reacting the dichloridite with a corresponding diol to arrive at the corresponding desired polyphosphite ligand. The condensation reactions are preferably carried out in the presence of a solvent, e.g. toluene, and an HCl acceptor, e.g. an amine, and may be carried out in a single-pot synthesis, if desired. For instance, desired symmetrical phosphite type ligands can be directly produced by reacting two mole equivalents of the phosphorochloridite intermediate of step (a) above with one mole equivalent of the diol.

Residual Wash Solvent

Any solvent that will (i) dissolve the crude polyphosphite crystals remaining after removal of the solvent, the first or primary solvent, used in the condensation reaction, and (ii) remove or reduce the amount of materials from the reaction that remain associated with the crystals, e.g., unreacted reagents, process aids, by-products, etc., can be used as the wash solvent. The first or primary solvent is typically an inert hydrocarbon such as toluene. At the completion of the condensation reaction and formation of the polyphosphite crystals, the first solvent is removed by any suitable means, e.g., distillation, to the fullest extent practically possible in terms of process efficiency and economics. Damp polyphosphite crystals in combination with whatever other materials were in the reaction mass at the time the condensation reaction was terminated remain with the polyphosphite crystals.

These damp crystals, along with the other remaining reaction mass materials, are then dissolved in the wash solvent. This solvent is typically an ester such as an alkyl acetate (e.g., ethyl acetate, propyl acetate, acetonitrile), chlorinated hydrocarbon, and it is chosen so as to (i) dissolve everything remaining after the removal of the first solvent, and (ii) selectively re-crystallize the polyphosphite ligand while leaving everything else, or most everything else, in solution. The polyphosphite ligand can be re-crystallized using known techniques and equipment. Typically the damp crystals are dissolved with a minimal amount of wash solvent at elevated temperature (typically >70° C.), and then slowly cooled (<20° C.) to effect recrystallization. Alternatively, another solvent can be added which has a dramatically lower solubility for the polyphosphite (such as a saturated alkane, e.g., hexane or a supersaturated $CO_2$) to effect precipitation. The precipitated crystals are then collected by filtration or centrifuge.

The recrystallized polyphosphite ligand is then dried using conventional drying equipment and techniques but will almost always retain more than 0.5 wt % wash solvent due solvent of crystallization. For example, the slurry of product is separated from the mother liquor by filtration (or centrifuge) and the solids either dried under vacuum in the filter or may be transferred to a conventional rotary tumble drier. The drying conditions are chosen to effect removal of solvent without decomposition thus typical conditions are a temperature of 20° C. to 100° C. and a pressure of less than atmospheric, preferably at the lowest absolute pressure possible in the equipment. A small inert gas purge (e.g., $N_2$) may be used to facilitate the drying process. Care is taken not to heat the damp crystals until most of the free liquid has evaporated to avoid melting the crystals. Typically the free solvent (i.e., solvent that is simply trapped between crystals) is removed quickly but the residual wash solvent is much more difficult to remove. While not being bound by theory, the residual wash solvent that is difficult to remove may be classical "solvent of crystallization" or solvent physically trapped inside crystals or crystal imperfections. To remove this residual wash solvent to <0.5 wt %, preferably less than 0.3 wt % and more preferably to less than 0.1 wt %, the crystals and residual solvent is mixed with a secondary alcohol.

Surprisingly, secondary alcohols have been found to effect removal of the residual wash solvent without (1) degrading the product, or (2) forming a new solvent of crystallization. Since the crude product typically has acidic impurities from hydrolysis of phosphorus trichloride ($PCl_3$) and similar intermediates, care must be taken to avoid acid-catalyzed decomposition of the product as described in US 2010/0267991 and U.S. Pat. Nos. 5,741,942 and 5,288,918. As shown in the '918 patent at column 24, primary alcohols are prone to acid-catalyzed decomposition of the ligand thus secondary alcohols are used. Presumably the steric bulk of the secondary alcohol inhibits the undesired alcoholysis reaction. While tertiary alcohols would be even better, they tend to have high boiling points or are solids and thus difficult to remove from the final product. Secondary alcohols cannot be used as the condensation solvent since they will react with $PCl_3$ and/or the phosphorochloridite intermediates but have been found to be useful after the wash solvent to remove the wash solvent. Secondary alcohols should be volatile enough to be readily removed in the available driers thus $C_3$-$C_6$ secondary alcohols such as isopropanol (IPA), cyclohexanol, 2-butanol, 2- or 3-pentanol, and the like (including mixtures thereof) are preferred. The most preferred is isopropanol being the least expensive and most readily vaporized solvent.

It has been surprisingly found that simply slurrying the damp crystals after the wash solvent step is effective in removing the residual wash solvent. The amount of secondary alcohol used to slurry the crystals can vary widely and to convenience, but typically only that amount is used to allow the crystals to completely slurry (suspending without necessarily dissolving) with the alcohol. In one embodiment, the amount of alcohol used is about one half the amount of wash solvent used. Depending on the extent of solvent of crystallization formation, gentle (<70° C.) and short-term heating (<2 hours) of the slurry without necessarily redissolving the crystals is sufficient to effect removal of the residual wash solvent. Since the polyphosphites are more susceptible to degradation in solution, time at elevated temperature should be minimized as there is no advantage to prolonged treatment. The vigor of agitation is not thought to be important (i.e., the crystals are not being ground up to any significant degree), just good contact with the alcohols solvent is needed. Cooling the mixture to effect as much precipitation as possible is preferred to minimize product losses. The resulting washed precipitate is collected on a filter or centrifuge and dried as before. Typically only a single treatment is needed (removing a sample of the damp solids and analyzing for residual wash solvent by GC or $^1$H NMR can be used to verify that the single treatment has been effective). This operation can be performed within some filter and centrifuge units as well, depending on equipment design, thus minimizing solid transfer issues.

During the wash solvent treatment, residual amine base from the previous coupling step is likely to be present. The residual base is typically a 3°-amine (e.g., triethylamine or pyridine). If traces of residual acid are thought to be present in the crude product crystals, small amounts of such amines may be optionally added to the secondary alcohol wash solvent to prevent alcoholysis. Typically this is <0.5 wt % based on the secondary alcohol, preferably <0.1 wt %. This is not normally required.

The invention is further described by the following examples. All parts and percentages are by weight unless otherwise specified. Temperatures are in ° C., and gas chromatograph (GC) an alysis of the crystals was performed by dissolving the solids in tetrahydrofuran (THF) with an internal standard. $^{31}$P NMR analysis was similarly performed in rigorously air- and peroxide-free THF or toluene (usually deuterated). Ion chromatography was performed by extracting the solid with de-ionized water and analyzing the water extract. Loss on drying (e.g., ASTM E1868-10) and color (APHA; ASTM D1209-05 (2011) in toluene) are standard industry methods.

SPECIFIC EMBODIMENTS

Example 1

Preparation of 6,6'-(3,3',5,5'-tetra-tert-butylbiphenyl-2,2'-diyl)bis(oxy)didibenzo-[d,f][1,3,2]-dioxaphosphepine Crude bisphosphite was prepared as described in WO2010/042313 A1. Using 250 kg 2,2'biphenol, 289 kg $PCl_3$ in 2,525 kg toluene (with 4 kg pyridine), a monochloridite is made. After removing excess $PCl_3$, 315 kg pyridine and 274 kg of 3,3',5,5'-tetra-tert-butyl-2,2'-biphenol (ISO-BHT, a bridging diol in 1550 kg toluene) are added and the resulting mixture is extracted with water to remove pyridinium hydrochloride salt. The resulting product is then recrystallized from ethyl or propyl acetate. A portion of the wet cake (73 kg) is mixed with 144.0 liters (L) isopropyl alcohol (IPA, degassed) in 250 L glass vessel. The contents are heated to 70-75° C. Degassed IPA (73 L) is further added to obtain a thinner solution and heated to 75° C. This is followed by cooling to ambient temperature (23° C.) within 2 hours. The resulting slurry is filtered in a centrifuge, washed twice with 73 L (each wash) of IPA, followed by spin drying for 45 minutes. The wet cake is then transferred to a 2 kiloliter (kL) rotary vacuum cone drier (RVD). The results of the drying are as follows:

Analysis of Material Taken Prior to Treatment:
$^{31}$P-NMR=97.13%
Others (Hydrolysis+oxidation products)=2.90%
GC impurity (ND=not detected; estimated detection limit=0.01 wt %):
  Toluene=ND;
  Ethyl acetate(EAc)=0.09%;
  n-propylacetate (NPA)=3.10%
  Pyridine=ND;
  2,2'-Biphenol=0.35%,
  SO BHT=0.03%
Weight of wet material taken for treatment=73 Kg
Weight of wet material after treatment=72 Kg
Analysis of Wet Material after IPA Treatment:
$^{31}$P-NMR=99.46%,
Others (Hydrolysis+oxidation products)=0.55%
GC impurity:
  Toluene=ND;
  EAc=ND;
  NPA=ND;
  IPA=11.63%,
  Pyridine=ND;
  2,2'=Biphenol=ND;
  ISO BHT=ND Table Example 1
Drying Conditions and Results

| Time (Hrs) | Drying Jacket Temperature | Inner Temp RVD (° C.) | Vacuum mbara | Impurities by GC | | | | | | | $^{31}$P-NMR | |
|---|---|---|---|---|---|---|---|---|---|---|---|---|
| | | | | Toluene | EAc | IPA | NP-Acetate | Pyridine | ISO BHT | 2'2 Biphenol | Product | Others |
| 24 | 75 | 68.5 | 2 | ND | ND | 0.16 | ND | ND | 0.01 | ND | 99.52 | 0.48 |

Wt. of dry material after unloading from RVD - 62.5 Kg

Analysis of Dry Material
LOD=0.10%
Description=White Powder
$^{31}$P-NMR Product=99.46%
Others=0.54%
Impurities by GC
  Diols=ND,
  EAc+IPA+NPAc+Toluene=0.13%,
  Pyridine=ND
Chloride Content IC=3 ppm
$H_3PO_3$ By IC=11 ppm
(Color) APHA=<70

The wet cake contained over 11% residual solvent yet dried to well below 0.5% residual solvent in 24 hours.

Comparative Example 1 (Production Scale)

Wet cake from commercial production (280 kg) is re-dissolved in hot, deaerated n-propylacetate, cooled to 10-15° C. and collected on a centrifuge. The damp crystals are then transferred to a rotary cone dryer. The drying results are reported below and in Table Comparative Example 1.

Analysis of material taken prior to reworking:
$^{31}$P-NMR=99.45
Others=0.55%
GC impurity:
  Toluene=0.62,
  Ethyl Acetate=8.68,
  Pyridine=0.03,
  2,2'-Biphenol=ND,
  ISO BHT=ND
Weight of wet material after reworking=272.8 Kg
$^{31}$P-NMR=99.45
Others=0.55%
GC impurity:
  Toluene=0.02,
  Ethyl Acetate=0.96,
  Pyridine=ND,
  2,2'-Biphenol=ND,
  ISO BHT=ND
  NP-acetate=10.38

Table Comparative Example 1
Drying Conditions and Results

| Time (Hrs) | Drying Jacket Temp | Inner Temp RVD | Vacuum (mbar) | Impurites by GC | | | | | | $^{31}$P-NMR | |
|---|---|---|---|---|---|---|---|---|---|---|---|
| | | | | Toluene | EAc | Pyridine | NP-acetate | ISO BHT | 2'2-Biphenol | Product | Others |
| 12 | 75 | 67.2 | 5 | 0.02 | 0.84 | ND | 8.76 | ND | ND | 99.36 | 0.64 |
| 36 | 75 | 67.2 | 5 | 0.02 | 0.78 | ND | 8.46 | 0.015 | ND | 99.48 | 0.53 |
| 48 | 75 | 68.0 | 4 | 0.02 | 0.94 | ND | 8.79 | 0.01 | ND | 99.42 | 0.59 |
| 60 | 75 | 68.1 | 4 | 0.01 | 0.84 | ND | 8.18 | ND | ND | 99.42 | 0.59 |
| 72 | 75 | 68.5 | 3 | 0.01 | 0.73 | ND | 7.71 | ND | ND | 99.43 | 0.58 |
| 84 | 75 | 68.5 | 3 | 0.31 | 0.55 | ND | 5.90 | ND | ND | 99.49 | 0.51 |
| 99 | 75 | 68.8 | 2 | 0.18 | 0.35 | ND | 3.71 | ND | ND | 99.35 | 0.65 |
| 115 | 75 | 69.0 | 2 | 0.48 | 0.30 | ND | 3.17 | ND | ND | 99.42 | 0.58 |
| 133 | 75 | 69.5 | 1 | 0.17 | 0.19 | ND | 1.90 | ND | ND | 99.43 | 0.57 |
| 155 | 75 | 69.5 | 1 | 0.17 | 0.14 | ND | 1.32 | ND | ND | 99.44 | 0.57 |
| 174 | 75 | 69.6 | 1 | 0.24 | 0.12 | ND | 1.10 | ND | ND | 99.45 | 0.55 |
| 186 | 78 | 72 | 1 | 0.16 | 0.12 | ND | 1.09 | 0.01 | ND | 99.45 | 0.56 |
| 198 | 78 | 72 | 1 | 0.09 | 0.11 | ND | 0.88 | ND | ND | — | — |
| 220 | 78.5 | 73 | 1 | 0.34 | 0.10 | ND | 0.81 | ND | ND | 99.51 | 0.49 |
| 244 | 78 | 72.1 | 1 | 0.31 | 0.09 | ND | 0.67 | ND | ND | 99.51 | 0.49 |
| 268 | 78 | 72.1 | 1 | 0.31 | 0.10 | ND | 0.74 | ND | ND | — | — |
| 274 | 78 | 72.1 | 1 | 0.23 | 0.10 | ND | 0.65 | ND | 0.01 | 99.39 | 0.62 |
| 288 | 82 | 75.2 | 1 | 0.17 | ND | ND | 0.63 | ND | ND | 99.45 | 0.55 |

-continued

Table Comparative Example 1
Drying Conditions and Results

| Time (Hrs) | Drying Jacket Temp | Inner Temp RVD | Vacuum (mbar) | Toluene | EAc | Pyridine | NP-acetate | ISO BHT | 2'2 - Biphenol | $^{31}$P-NMR Product | Others |
|---|---|---|---|---|---|---|---|---|---|---|---|
| 310 | 83 | 75.4 | 1 | 0.17 | ND | ND | 0.58 | ND | 0.01 | 99.51 | 0.49 |
| 334 | 83 | 75.5 | 1 | 0.12 | ND | ND | 0.54 | 0.01 | 0.02 | 99.53 | 0.47 |
| 346 | 83 | 75.5 | 1 | 0.11 | ND | ND | 0.51 | 0.02 | 0.05 | 99.39 | 0.62 |
| Wt. of dry material after unloading from RVD = 115.0 Kg (After 346 hrs 2,2 Biphenol and ISOBHT increased so unload the material) | | | | 0.12 | ND | ND | 0.54 | 0.04 | 0.12 | 99.38 | 0.63 |

For 72 hours of drying, the rate of decrease in n-propyl acetate percent is very low. Material (130 kg) is unloaded from RVD and drying of the remaining 142.8 kg material in RVD drying continued.

Despite very good vacuum and higher temperatures than Example 1, this system still failed to remove solvents to below a total of 0.5% and the material was beginning to degrade under these harsh conditions (the diols content was increasing).

Comparative Example 2

Drying data for material purified in ethyl acetate. Material from a commercial production run after initial ethyl acetate purification is re-dissolved in hot ethyl acetate, cooled to re-deposit crystals, isolated in a centrifuge, and removed to a 1.5 kL rotary drier. Weight. of wet material taken=98.20 kg.
Analysis of Material Taken Prior Drying:
31P-NMR=98.33%
Others=1.69%
Ethyl Acetate by Proton NMR=6.90%
Water=0.08%
LOD=9.08%
GC Impurities
  Toluene=0.01%
  EAc=8.81%
  Pyridine=ND,
  2,2'-Biphenol=ND,
  ISO BHT=ND Re-crystallizing a second time from ethyl acetate gave the same results as the initial re-crystallization in that after 138 hours, the material still had well over 0.5% residual solvents.

Comparative Example 3: Small Scale Propylacetate Re-Crystallization

Similar to the above, a small batch of crude bisphosphite product is re-purified in laboratory scale equipment. Damp material (2 kg) produced in the commercial scale equipment is treated with 4 L N-propyl acetate (degassed) and heated to 72-75° C., stirred for 15 minutes, and cooled to 10-15° C. in 3 hours. The resulting crystals are collected on a centrifuge and washed with two 2 L cold N-Propyl acetate, spun dry, and then transferred to a 15 L rotary dryer.
Analysis of Wet Cake Taken Prior to Trial:
$^{31}$P-NMR=99.45
Others=0.55%
GC impurity:
  Toluene=0.62%,
  Ethyl Acetate=8.68%,
  Pyridine=0.03%,
  2,2'-Biphenol=ND,
  ISO BHT=ND
Weight of recovered wet cake=1.86 kg
Analysis of Wet Cake after Purification:
LOD=10.90%
$^{31}$P-NMR=99.46
Others=0.55%
Weight of material after drying=1.60 Kg Table Comparative Example 2
Drying Conditions and Results

| Time (Hrs) | Drying Jacket temp | Inner Temp RVD | Vacuum | Toluene | EAc | Pyridine | ISOBHT | 2'2 - Biphenol | LOD % w/w | $^{31}$P-NMR Product | Others |
|---|---|---|---|---|---|---|---|---|---|---|---|
| 14 | 80 | 72 | 2 mbar | ND | 5.39 | ND | ND | ND | 3.12 | 97.99 | 2.05 |
| 26 | 80 | 72 | 2 mbar | ND | 3.03 | ND | 0.02 | ND | — | 98.02 | 2.02 |
| 38 | 80 | 72 | 2 mbar | ND | 2.27 | ND | ND | ND | 1.16 | 98.16 | 1.88 |
| 62 | 80 | 73.1 | 1 mbar | 0.27 | 2.10 | ND | ND | ND | 1.50 | — | — |
| 78 | 80 | 73.2 | 1 mbar | 0.18 | 1.12 | ND | ND | ND | 0.41 | 98.11 | 1.93 |
| 90 | 80 | 73.2 | 1 mbar | 0.26 | 1.32 | ND | 0.03 | ND | 0.61 | 98.07 | 1.97 |
| 102 | 80 | 73.4 | 1 mbar | 0.16 | 1.30 | ND | ND | ND | 0.10 | 98.17 | 1.87 |
| 114 | 80 | 73.2 | 1 mbar | 0.17 | 1.20 | ND | ND | ND | 0.09 | 97.89 | 2.16 |
| 126 | 80 | 73.5 | 1 mbar | 0.18 | 1.10 | ND | ND | ND | 0.21 | 98.03 | 2.01 |
| 138 | 80 | 73.2 | 1 mbar | 0.12 | 0.96 | ND | 0.03 | 0.02 | 0.20 | 98.05 | 1.99 |

This example shows that in small laboratory or pilot plant equipment, the solvent is readily removed (over about 34 hours) in contrast to commercial equipment where after 300+ hours drying under more vigorous conditions failed to achieve acceptable solvent levels.

The Toluene content is very high and not dropping at an acceptable rate.

After 60 hours of drying it is clear that a different solvent of crystallization has formed, this time with toluene. The ethyl acetate and propyl acetate are also still strongly present and are not dropping at an acceptable rate.

Table Comparative Example 3
Drying Conditions and Results

| Time (Hrs) | Drying Jacket Temp | Inner Temp RVD (°C.) | Vacuum (mmHg) | Toluene | EAc | Pyridine | NP-acetate | ISO BHT | 2'2-Biphenol | LOD % w/w | ³¹P-NMR Product | Others |
|---|---|---|---|---|---|---|---|---|---|---|---|---|
| 12 | 80 | 70 | 720 | ND | 0.08 | ND | 0.96 | ND | ND | 0.53 | 99.42 | 0.58 |
| 20 | 80 | 70 | 720 | 0.01 | 0.06 | ND | 0.61 | 0.02 | ND | 0.28 | — | — |
| 28 | 80 | 70 | 720 | ND | 0.05 | ND | 0.50 | ND | ND | 0.12 | 99.40 | 0.61 |
| 34 | 80 | 70 | 720 | ND | 0.05 | ND | 0.43 | ND | ND | 0.10 | 99.46 | 0.54 |

Comparative Example 4: Toluene Re-Crystallization

Material is re-crystallized from toluene in place of propyl acetate as described in Comparative Example 3. Wet cake (2 kg) is mixed with 4 L toluene (degassed) and heated to 60-65° C. A clear solution is observed. After stirring for 15 minutes, the solution is cooled to 0-5° C. in 3 hours. A centrifuge is used to collect the crystals (no washes are used). The material is then transferred to a 15 L rotary drier and the drying results shown below.

Analysis of Material Taken Prior to Re-Crystallization:
LOD=9.08%
$^{31}$P-NMR=98.21%
Others=1.81%
EAc by Proton NMR=6.90%
GC impurity:
Toluene=0.01%,
Ethyl Acetate=8.81%,
Pyridine=ND,
2,2'-Biphenol=ND,
ISO BHT=ND
Weight of recovered wet material=1.66 kg
Analysis of Wet Cake after Purification:
LOD=9.60%
$^{31}$P-NMR=97.86%
Others=2.19%
EAc by Proton NMR=0.80
GC impurity:
Toluene=8.89%,
Ethyl Acetate=0.94%,
Pyridine=ND,
2,2'-Biphenol=ND,
ISO BHT=ND
Weight of material after drying=1.55 Kg

Comparative Example 5

A pilot plant run uses the process described in WO 2010/042313A1 based on 20 kg 2,2'biphenol, 23.2 kg PCl$_3$, 0.3 kg pyridine, and 160 kg toluene in the first step and 25 kg pyridine and 21.9 kg ISO BHT diol (in 110 kg toluene) in the second step. The resulting crude product is purified by charging 170.0 L ethyl acetate and heated to 72-75° C. The solution is not completely clear. The mixture is cooled to 25-27° C. in 2 hours and then further cooled to 0-5° C. in 1 hour. The material is collected on a centrifuge and washed with 170.0 L chilled ethyl acetate. The resulting wet cake is transferred to a 15 L rotary dryer. The wet material is dried for 2 hours at ambient temperature (23° C.) and then at 60-65° C. for 24 hours where loss on drying (LOD) is less than 0.5%. The yield was 32.70 kg initial wet cake, 29.60 kg dried material.

This demonstrates that the small scale equipment does not exhibit the phenomenon with ethyl acetate (compare to Comparative Example 2).

What is claimed is:

1. A process for removing a residual wash solvent selected from the group consisting of alkyl ester, acetonitrile and chlorinated hydrocarbon from undissolved polyphosphite crystals of formula (i)

Table Comparative Example 4
Drying Conditions and Results

| Time (Hrs) | Drying Jacket Temp | Inner Temp RVD | Vacuum (mmHg) | Toluene | EAc | Pyridine | NP-acetate | ISO BHT | 2'2-Biphenol | LOD % w/w | ³¹P-NMR Product | Others |
|---|---|---|---|---|---|---|---|---|---|---|---|---|
| 12 | 80 | 70 | 720 | 7.50 | 0.67 | ND | 0.39 | 0.01 | ND | 8.24 | 97.89 | 2.16 |
| 24 | 80 | 70 | 720 | 6.46 | 0.50 | ND | 0.51 | ND | ND | 7.50 | 97.90 | 2.15 |
| 36 | 80 | 70 | 720 | 5.77 | 0.48 | ND | 0.55 | ND | 0.02 | 6.39 | 97.91 | 2.13 |
| 48 | 80 | 70 | 720 | 4.90 | 0.40 | ND | 0.56 | ND | ND | 6.80 | 97.86 | 2.19 |
| 60 | 80 | 70 | 720 | 5.10 | 0.36 | ND | 0.64 | ND | ND | — | 97.90 | 2.14 |

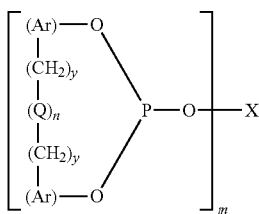 (i)

wherein each Ar group represents an identical or different substituted or unsubstituted aryl radical; wherein X represents a m-valent radical selected from the group consisting of alkylene, alkylene-oxy-alkylene, arylene, and arylene-$(CH_2)y$-$(Q\text{-})_n$-$(CH_2)y$-arylene-, wherein each arylene radical is Ar; wherein each y individually has a value of 0 or 1; wherein each Q individually represents a divalent bridging group selected from the class consisting of —$CR_1R_2$—, —O—, —S—, —$NR_3$—, —$SiR_4R_5$— and —CO—, wherein each $R_1$ and $R_2$ radical individually represents a radical selected from the group consisting of hydrogen, alkyl of 1 to 12 carbon atoms, phenyl, tolyl and anisyl, wherein each $R_3$, $R_4$, and $R_5$ radical individually represents —H or —$CH_3$; wherein each n individually has a value of 0 or 1; and wherein m has a value of 2 to 6;

the process comprising the steps of:
A. slurrying the undissolved polyphosphite crystals and residual wash solvent with a $C_3$-$C_6$ secondary alcohol to form a mixture of undissolved polyphosphite crystals, residual wash solvent and $C_3$-$C_6$ secondary alcohol, and
B. Drying the mixture at a temperature from 20° C. to 100° C. and a pressure less than 760 mmHg (101.325 kPa)
  (i) to remove the residual wash solvent and $C_3$-$C_6$ secondary alcohol to a content of less than 0.5 wt % based on the weight of the polyphosphite crystals
  (ii) without degrading the polyphosphite crystals or forming a new solvent of crystallization.

2. The process of claim 1 comprising the further step of separating the polyphosphite crystals from the residual wash solvent and $C_3$-$C_6$ secondary alcohol before drying the crystals to a content of less than 0.5 wt % based on the weight of the polyphosphite crystals.

3. The process of claim 2 in which the crystals are separated from the residual wash solvent and $C_3$-$C_6$ secondary alcohol by centrifugation or filtration.

4. The process of claim 3 in which the residual wash solvent is ethyl or propyl acetate.

5. The process of claim 4 in which the polyphosphite is a bisphosphite.

6. The process of claim 1 in which the $C_3$-$C_6$ secondary alcohol is isopropyl alcohol.

* * * * *